United States Patent
Chaubet et al.

(10) Patent No.: US 6,646,120 B1
(45) Date of Patent: Nov. 11, 2003

(54) DEXTRAN DERIVATIVES, PREPARATION AND MEDICINAL APPLICATIONS

(75) Inventors: Frederic Chaubet, Eaubonne (FR); Remi Huynh, Saint-Amand-les-Eaux (FR); Latifa Dahri, Saint-Amand-les-Eaux (FR); Jose Correia, Saint-Amand-les-Eaux (FR); Marcel Jozefowicz, Lamorlaye (FR); Jacqueline Jozefonvicz, Lamorlaye (FR)

(73) Assignee: Biodex, St. Amand les Eaux (FR)

( * ) Notice: Subject to any disclaimer, the term of this patent is extended or adjusted under 35 U.S.C. 154(b) by 0 days.

(21) Appl. No.: 09/367,111

(22) PCT Filed: Dec. 11, 1998

(86) PCT No.: PCT/FR98/02699

§ 371 (c)(1),
(2), (4) Date: Sep. 26, 2000

(87) PCT Pub. No.: WO99/29734

PCT Pub. Date: Jun. 17, 1999

(30) Foreign Application Priority Data

Dec. 11, 1997 (FR) ............................................ 97 15702

(51) Int. Cl.⁷ ...................... C08B 37/02; A61K 31/715; A61K 31/725
(52) U.S. Cl. ............................ 536/51; 514/12; 530/399
(58) Field of Search ................................ 536/112, 124; 514/59, 12; 530/399

(56) References Cited

PUBLICATIONS

Chaubet, Frederic et al "Synthesis and structure–anticoagulant property relationships of functionalized dextrans: CMDBS" Carbohydrate Polymers, 1996, 1995, 28(2), 145–52.*

* cited by examiner

*Primary Examiner*—James O. Wilson
*Assistant Examiner*—Ganapathy Krishnan
(74) *Attorney, Agent, or Firm*—Lowe Hauptman Gilman & Berner LLP

(57) ABSTRACT

The invention concerns dextran derivatives, their applications as medicines with specific biological action, and their preparation method. Said derivatives correspond to the general formula $DMC_aB_bSU_cS_d$, in which: D represents a polysaccharide chain, preferably consisting of sequences of glucoside units, MC represents methylcarboxylate groups, B represents carboxymethylbenzylamide groups, Su represents sulphate groups, S represents sulphonate groups, a, b, c and d represent the degree of substitution (ds), respectively in groups, MC, B, Su and S; a being equal to 0 or ≧0.3, b being equal to 0 or ≧0.1, c being equal to 0 or ≧0.1 and d being equal to 0 or ≧0.1 provided that when d=0, a and/or b are not equal to 0, said products having homogeneity of chain size distribution, illustrated by a gauss elution profile symmetrical in high performance steric exclusion chromatography, and homogeneity in the distribution of charged chemical groups, illustrated by an elution profile with a single symmetrical peak in low pressure ion-exchange chromatography.

14 Claims, 3 Drawing Sheets

1

DEXTRAN DERIVATIVES, PREPARATION AND MEDICINAL APPLICATIONS

This application claims priority from PCT/FR98/02699 filed Dec. 11, 1998, and from French patent application 97/15702 filed Dec. 11, 1997.

The present invention relates to dextran derivatives, and to their applications as medicines with specific biological action, such as a cicatrizing action, an anti-complement action (substitute for plasma), a proliferation modulating action or an anticoagulant action, and more specifically an anti-thrombotic action, as well as to a process for their preparation.

Various dextrans substituted with side chains bearing carboxylate and sulfonate groups have been described. In particular, French patent 2,461,724 and French patent 2,555,589 describe dextrans substituted with said groups, which respectively display anticoagulant properties and anticoagulant and anti-inflammatory properties; European patent 0,402,194 describes the cell and tissue regeneration properties of such substituted dextrans.

It has also been shown that such substituted dextrans can have other biological activities, depending on the degree of substitution with said groups; in particular, European patent 0,514,449 describes dextrans (D) substituted with carboxymethyl (CM) and carboxymethylbenzylamide sulfonate (BS) groups of general formula $D_X CM_Y BS_Z$, in which X, which represents the average number of unsubstituted saccharide units per 100 saccharide units, is less than or equal to 50, Y, which represents the average number of carboxymethyl groups per 100 saccharide units, is between 10 and 90, and Z, which represents the average number of carboxymethylbenzylamide sulfonate groups per 100 saccharide units, is between 15 and 35; to give an agent for inhibiting the growth of tumor cells.

These various derivatives, the structure of which is summarized in FIG. 1, are generally obtained by random substitution of dextran with three different groups: carboxymethyl (CM), carboxymethylbenzylamide (B) and carboxymethylbenzylamide sulfonate (S) (sulfonation on the aromatic ring with chlorosulfonic acid).

More specifically:

a) the carboxymethylation of dextran (production of CMD) is carried out in basic aqueous medium, by the action of monochloroacetic acid. Three successive carboxymethylation reactions are required to obtain a degree of substitution (ds) of the dextran, expressed relative to the number of free hydroxyl functions in a glucoside unit of the dextran, of between 0.7 and 1.1;

b) the coupling of benzylamine to the carboxymethyl groups (production of CMDB) is based on the ability of the carboxylate function to form an unstable mixed anhydride capable of reacting with a reagent bearing a primary amine function (R—NH$_2$). Two different processes or activation reactions were used to achieve the formation of a mixed anhydride:
  action of isobutyl chloroformate (IBC) or
  action of N-ethoxycarbonyl-2-ethoxy-1,2-dihydroquinoline (EEDQ).

In both cases, the reaction is carried out in a heterogeneous medium: water/dimethylformamide or water/ethanol, respectively.

These two coupling processes give similar degrees of substitution (ds), of about 0.08 to 0.12, in a single step. In the case of coupling with EEDQ, the ds can reach 0.25 to 0.30, in a single step, when the intermediate product is activated at a temperature of 30 to 40° C.

As with the carboxymethylation, to achieve high ds values for benzylamine, it is not possible to increase the concentrations of the various reagents. It is thus necessary to perform successive couplings in order to improve the reaction yield. The CMDB precipitated, washed and dried after the first coupling undergoes a second and/or a third coupling under exactly the same conditions as the first, without consideration of the substitutions due to the first coupling.

c) the sulfonation or sulfation takes place by the action of monochlorosulfonic acid on the CMDB, in anhydrous organic medium (for example dichloromethane) and in heterogeneous phase, the CMDB not being soluble in dichloromethane. In such a heterogeneous medium, the distribution of the sulfates in the saccharide units occurs unequally (Ricketts, C. R., J. Chem. Soc., 1956, 3752–3756). It is necessary to perform the reaction in excess monochlorosulfonic acid, while at the same time avoiding acid hydrolysis of the polysaccharide chain.

The [HSO$_3$Cl]/[bound B units] ratios for the CMDBs and [HSO$_3$Cl]/[free OH] ratios for the CMD range between 0.8 and 3.

In order essentially to obtain a sulfonation of the aromatic rings (B units), the [HSO$_3$Cl]/[bound B units] molar ratio should be equal to 3, whereas, in order to obtain a sulfation of the hydroxyl functions borne by the glucoside units (production of sulfate functions), the [HSO$_3$Cl]/[free OH] molar ratio is about 1. In any case, the concentration of chlorosulfonic acid in the reaction medium should not exceed 0.15 M. Under these conditions, the percentage of units bearing a sulfonate function depends on the percentage of units substituted with benzylamide groups. A recent study (Maiga-Revel O. et al., Carbohydrates Polymers, 1997, 32, 89–93) has shown that the anticoagulant activity of the CMDSu (=carboxymethyldextran sulfate) and CMDBS (=carboxymethyldextran benzylamide sulfonate) dextran derivatives of the prior art depends on their sulfur content; however, CMDBSs have better anticoagulant activity than that obtained with CMDSu's, for an identical sulfur content.

The dextran derivatives obtained under the conditions defined above have the drawback of having irregular distribution of the chemical groups and of the sizes of the polysaccharide chains, leading to a heterogeneous final product whose properties are difficult to control.

The inventors have developed a novel process for preparing dextran derivatives, which allows better control of the production of specifically defined products (controllable degree of substitution, homogeneity of the distribution of the charged or uncharged chemical groups and size homogeneity of the polysaccharide chains in the final product, selection and better reproducibility of the desired activity).

A subject of the present invention is dextran derivatives of general formula $DMC_a B_b Su_c S_d$, in which:
  D represents a polysaccharide chain, preferably consisting of concatenations of glucoside units,
  MC represents methylcarboxylate groups,
  B represents carboxymethylbenzylamide groups,
  Su represents sulfate groups (sulfation of the-free hydroxyl functions borne by the glucoside units),
  S represents sulfonate groups (sulfonation of the aromatic rings),
  a, b, c and d represent the degree of substitution (ds), expressed relative to the number of free hydroxyl functions in a dextran glucoside unit, with groups MC, B, Su and S, respectively; a being equal to 0 or $\geq 0.3$, b being equal to 0 or $\geq 0.1$, c being equal to 0 or $\geq 0.1$ and d being equal to 0 or $\geq 0.15$, with the proviso that when d=0, a and/or b are $\neq 0$, which products display:
- homogeneity of the size distribution of the chains, illustrated by an elution profile of symmetrical Gaussian type in high performance steric exclusion chromatography, and
- homogeneity of the distribution of charged chemical groups, illustrated by an elution profile as a single symmetrical peak in low-pressure ion exchange chromatography.

These products are considered as being copolymers consisting of fictive subunits R—OH and R—OX, it being possible for X to be a methylcarboxylate (MC) benzylamide (B), sulfate (Su) or sulfonate (S) group, the polysaccharide chain of the unsubstituted dextran being considered as consisting of 300 fictive R—OH subunits, instead of 100 glucoside units, with regard to the fact that an unsubstituted glucoside unit comprises three free hydroxyl groups. Thus, a dextran methylcarboxylate (DMC) with a degree of substitution (ds) with methylcarboxylate groups of 1.2 contains 1.20 substituted groups (R—MC) and 1.80 free hydroxyl groups (R—OH), per glucoside unit.

This thus gives, in contrast with the heterogeneous products of the prior art, homogeneous products, of targeted composition, in which the bioactive chemical groups are distributed along the macro-molecular chains in a specific order, giving the product a biological property which will not be found in a product of the same overall composition but in which the distribution of said groups along the macromolecular chains is different (different preparation, in particular).

In other words, in the dextran derivatives according to the invention, the distribution of the chemical groups gives the final product a specific biological property; the consequence of such a distribution is that the chemical composition of each polysaccharide chain is identical to the overall chemical composition of the product. Accordingly, there is an optimum chemical composition for a maximum specific biological activity; there is thus a direct relationship between the biological property considered and the overall chemical composition of the product.

For example:
- the dextran derivatives of general formula $DMC_aB_bSu_cS_d$ as defined above, in which $a \geq 0.6$, $b \neq 0$, c equal to 0 or $\leq 0.5$ and $d \leq 0.15$ or d equal to 0 are essentially cicatrizing agents, preferably when they have a molar mass between 3000 and 500,000 g/mol; the dextran derivatives preferred as cicatrizing agents are those in which a is between 0.7 and 0.9; $c \leq 0.5$ and $d \leq 0.15$ or equal to 0;
- the dextran derivatives of general formula $DMC_aB_bSu_cS_d$ as defined above, in which $a \geq 0.3$, $b \neq 0$, c equal to 0 or $\leq 0.4$ and $d \leq 0.15$ or equal to 0 are essentially agents with anti-complement activity and plasma substitutes, preferably when they have a molar mass of between 10,000 and 60,000 g/mol; the dextran derivatives preferred as agents with anti-complement activity and as substitutes for plasma are those in which a is between 0.40 and 1.15, $b \leq 0.4$, $c \leq 0.2$ and $d \leq 0.15$ or equal to 0;
- the dextran derivatives of general formula $DMC_aB_bSu_cS_d$ as defined above, in which $a \geq 0.5$, $b \neq 0$, c equal to 0 or $\leq 0.4$ and $d \leq 0.15$ are essentially agents for modifying cell proliferation, preferably when they have a molar mass of between 3000 and 100,000 g/mol; the dextran derivatives preferred as cell proliferation modulating agents are those in which a is between 0.5 and 1.2; b is between 0.2 and 0.6; c is between 0.1 and 0.4 and $d \leq 0.15$ or equal to 0; and
- the dextran derivatives of general formula $DMC_aB_bSu_cS_d$ as defined above, in which $a \geq 0.4$, $c \geq 0.3$ and $d \leq 0.15$ or equal to 0 are essentially anticoagulant agents, preferably when they have a molar mass of between 3000 and 20,000 g/mol and a value for $b \neq 0$.

A subject of the present invention is also medicines, characterized in that they comprise as active principle at least one dextran derivative as defined above, optionally combined with another active principle and/or with at least one pharmaceutically acceptable vehicle and/or a physiologically acceptable support, preferably a liposome.

The combined active principles are chosen from the group comprising dextrans, growth factors (for example an acidic fibroblast growth factor (FGF) or a basic FGF), local anesthetics, anti-infection agents, seric proteins and collagen.

A subject of the present invention is also a process (process 1) for preparing dextran derivatives of general formula $DMC_aB_bSu_cS_d$, as defined above, characterized in that it comprises the following steps:
a) carboxymethylation comprising (i) activation of an unsubstituted dextran, by placing said dextran in contact with a basic two-phase liquid aqueous-alcoholic medium for at least 1 h with stirring, (ii) addition of monochloroacetic acid to the activated product obtained, at a temperature of between 40 and 90° C., preferably at 60° C., the ratio $R_{MC}$, equal to the number of moles of monochloroacetic acid/number of moles of OH, being between 0.3 and 2, (iii) isolation and optionally purification of the dextran methylcarboxylate (DMC) obtained.
b) coupling of benzylamine with methylcarboxylate groups (benzylamidation) comprising (i) the placing in contact, for at least 2 h and in an acidic aqueous medium, of the DMC obtained in a) with a primary amine (benzylamine), in the presence of a water-soluble carbodiimide such as 1-cyclohexyl-3-(2-morpholinoethyl)carbodiimide meta-p-toluene sulfonate (CMC) or 1-ethyl-3-(3-dimethylaminopropyl) carbodiimide hydrochloride (EDC) as coupling agent, at a temperature of between 0° C. and 30° C., the CMC/MC molar ratio being between 0.25 and 2 and the benzylamine/MC molar ratio being between 0.25 and 2, (ii) isolation of the dextran methylcarboxyl benzylamide (DMCB) obtained and optionally purification thereof.

Such a step, performed in homogeneous medium and in the presence of a water-soluble carbodiimide as coupling reagent, allows better control of the reaction and thus preparation of the final product, this product having a homogeneity of the chain size distribution, illustrated by an elution profile of symmetrical Gaussian type in high performance steric exclusion chromatography and a homogeneity of the distribution of charged chemical groups, illustrated by an elution profile as a single symmetrical peak in low-pressure ion exchange chromatography.

c) sulfation comprising (i) the formation of a trialkylammonium salt of the DMCB obtained in b), (ii) solubilization of the salt obtained in an anhydrous polar solvent, generally a Lewis base (electron donor), such as dimethyl sulfoxide (DMSO) or dimethylformamide (DMF) and (iii) addition, to said dissolved salt, of a complex based on sulfur trioxide such as $SO_3$-pyridine, $SO_3$-triethylamine or $SO_3$-DMF dissolved in the same solvent, at a temperature of less than 70° C., the complex based on sulfur trioxide/free OH molar ratio being between 0.25 and 12, and optionally d) sulfonation of the groups B by mixing, with stirring, a derivative DMCBSu in suspension in an anhydrous solvent with chlorosulfonic acid dissolved in the same solvent, at a temperature between room temperature and the boiling point of the solvent used.

Unexpectedly, the process according to the invention allows the degree of substitution of the dextran to be controlled, in a number of steps which is significantly smaller than the number of steps in the processes of the prior art, to give products with an elution profile of symmetrical Gaussian type in high performance steric exclusion chromatography and an elution profile as a single symmetrical peak in low-pressure ion-exchange chromatography and the desired biological activity, with yields which are significantly higher than those of the prior art.

In addition, the process according to the invention makes it possible to reproducibly synthesize a product of desired chemical composition for the biological property selected. Thus, a biological activity preferably corresponds to a given chemical composition of a product.

For example, step a) gives, in a single step, a ds with MC of 1.0±0.1 per glucoside unit and a yield of greater than or equal to 80%, for an $R_{MC}$ value=0.85, in a water/tert-butanol or water/isopropanol (15/85 v/v) mixed medium, with stirring for 2 hours at 60° C.; starting with a DMC with a ds with MC=1, for a CMC/MC molar ratio of 0.75 and a benzylamine/MC molar ratio of 1, and with stirring at room temperature for 16 hours, step b) gives a DMCB product which has a ds with MC of 0.70±0.05 and a ds with B of 0.30±0.03, with a yield of greater than 80%; and step c) gives a yield of greater than or equal to 60%.

According to one advantageous embodiment of said process, in step a), the water/alcohol ratio is between 10/90 (v/v) and 25/75 (v/v) and is preferably 15/85 (v/v).

As a variant, the process (process 2) for preparing the dextran derivatives of general formula $DMC_aB_bSu_cS_d$, as defined above, in which a=0 or a≠0, b is other than 0 and d=0, comprises the following steps:

a) preparation of N-methylphenyl-2-chloroacetamide by placing a benzylamine in contact with chloroacetyl chloride, followed by isolation and purification of the product, b) placing dextran, dissolved in basic aqueous-alcoholic solution, in contact successively with N-methylphenyl-2-chloroacetamide in alcoholic solution obtained in a) in the presence or absence of monochloroacetic acid in alcoholic solution, maintaining the mixture obtained at a temperature above 40° C., preferably at 60° C., followed by isolation and optionally purification of the DB or DMCB obtained, and c) sulfation of the product obtained in b) comprising (i) formation of a trialkylammonium salt, (ii) dissolution of the salt obtained in an anhydrous polar solvent, generally a Lewis base, such as dimethyl sulfoxide (DMSO) or dimethylformamide (DMF), (iii) addition, to said dissolved salt, of a complex based on sulfur trioxide such as $SO_3$-pyridine, $SO_3$-triethylamine or $SO_3$-DMF dissolved in the same solvent, at a temperature below 70° C., the complex based on sulfur trioxide/free OH molar ratio being between 0.25 and 12, and (iv) isolation and optionally purification of the DBSu or DMCBSu obtained.

The presence of steps b) and c) above makes it possible to obtain the same homogeneity of the final product as that obtained with process 1 above.

In order to prepare the dextran derivatives of general formula $DMC_aB_bSu_cS_d$, as defined above, in which a is other than 0, b=0 and d=0 (→DMCSu) (process 3), said process is characterized in that it comprises the following steps:

a) carboxymethylation of an unsubstituted dextran, under the conditions outlined above, and b) sulfation of the DMC obtained in a) under the conditions outlined above.

Besides the preceding arrangements, the invention also comprises other arrangements, which will emerge from the description which follows, with reference to examples for carrying out the process which is the subject of the present invention, as well as to the attached drawings, in which:

FIG. 1 schematically illustrates the structure of a dextran substituted with various chemical groups attached to the glucoside units; the position of the substituent on the various carbons of the glucoside base units is shown in 2, by way of example;

Figure 1:
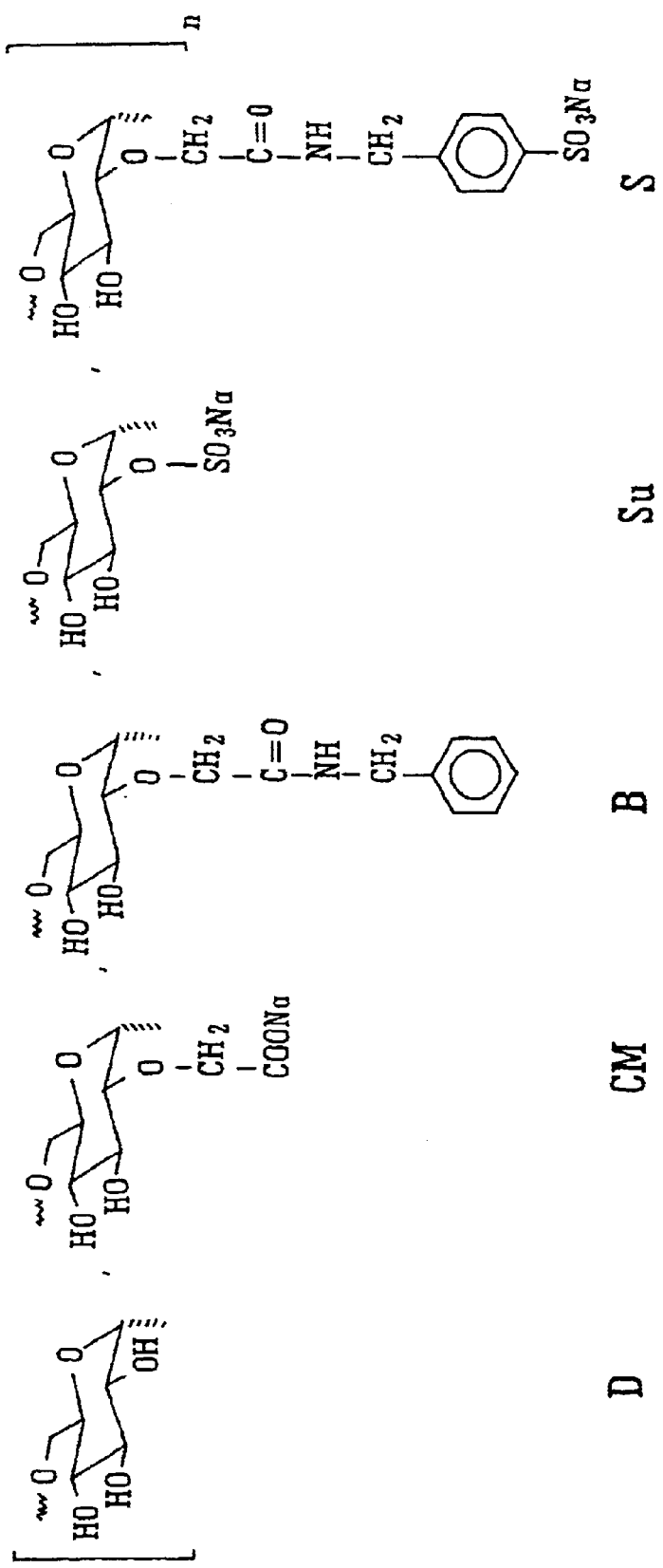
Figure 2:
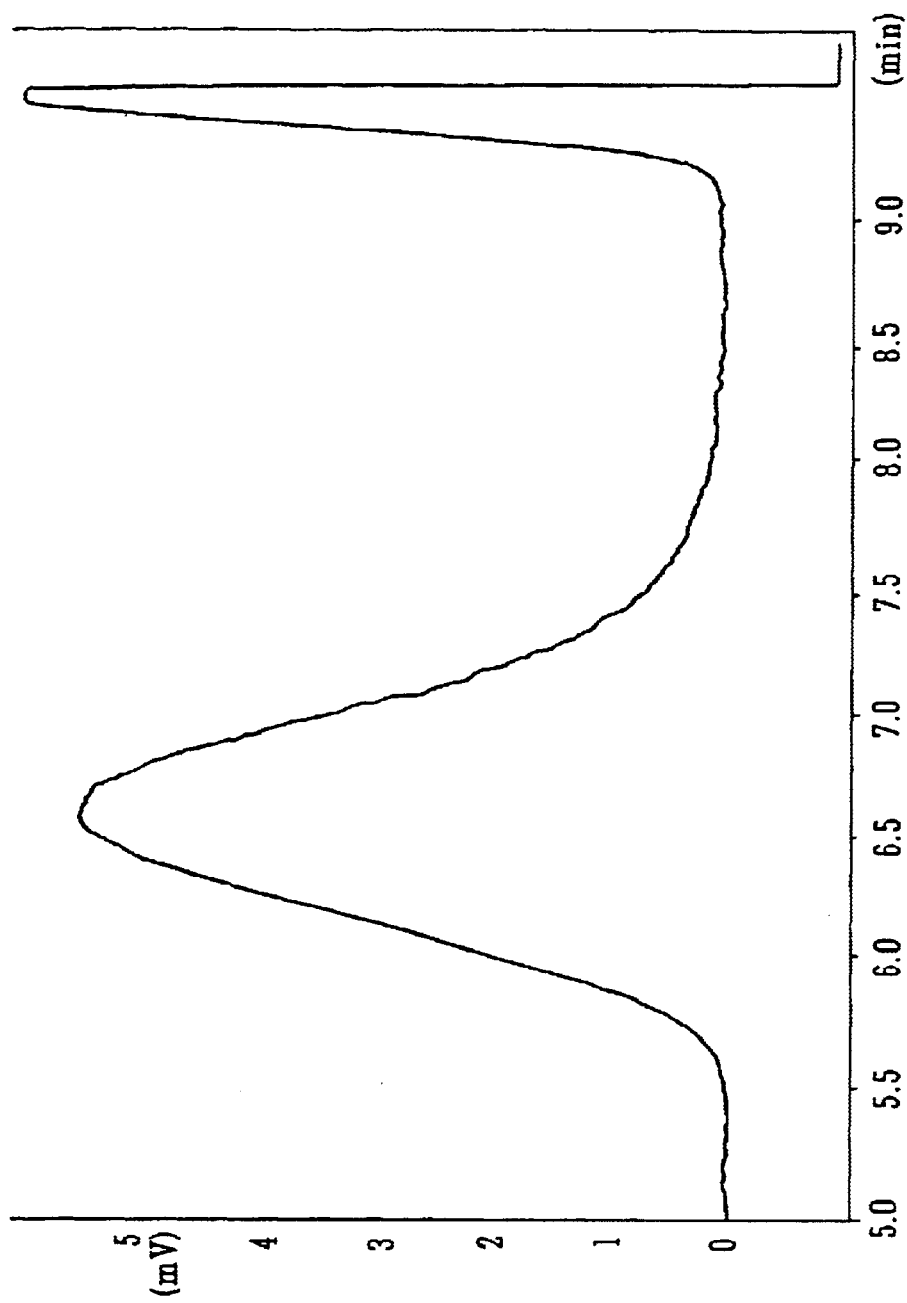
FIG. 2 illustrates the high performance steric exclusion chromatogram obtained with a dextran derivative as defined above (DMCBSu)
Figure 3:
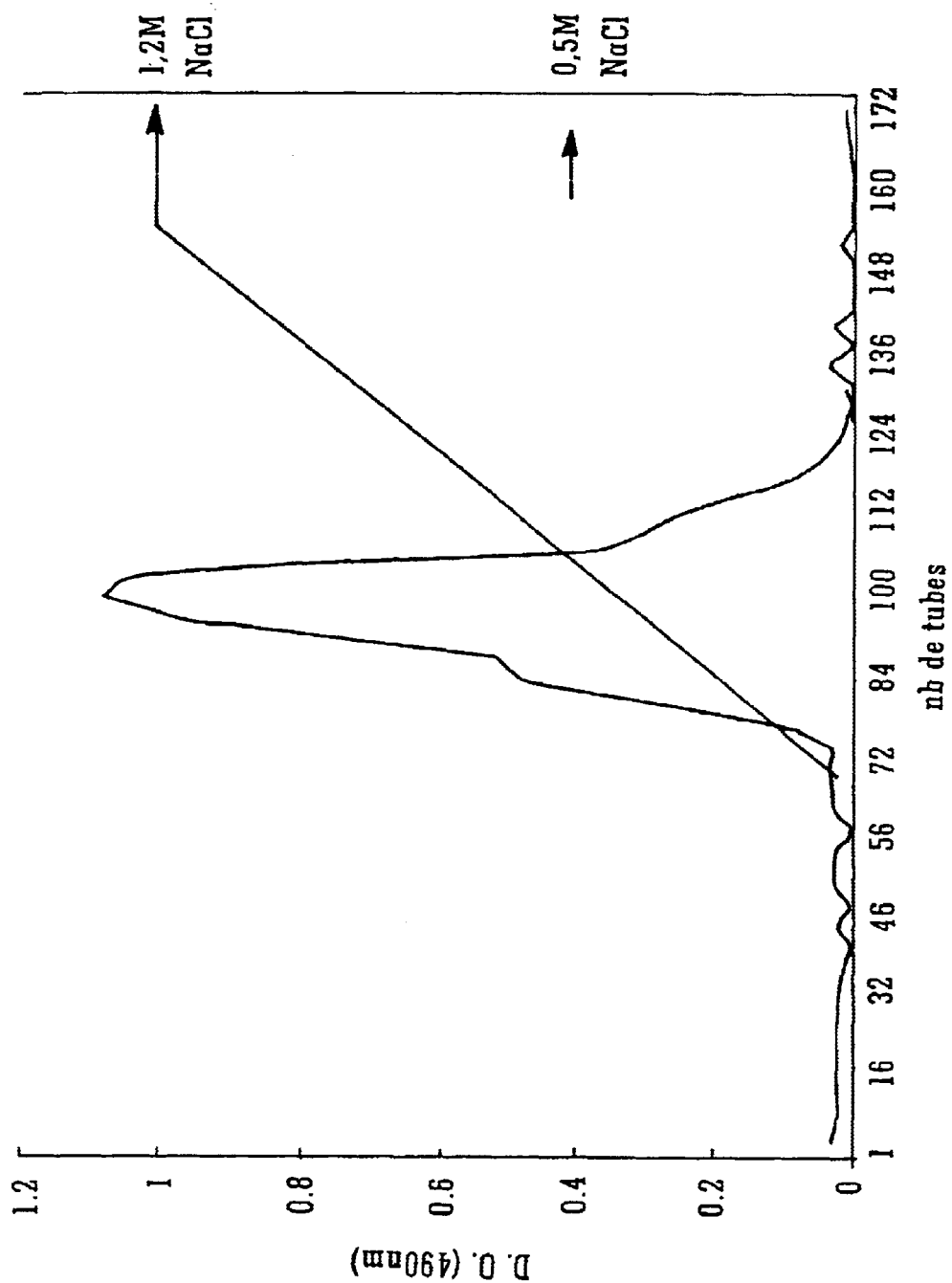
FIG. 3 illustrates the ion-exchange chromatogram obtained with a dextran derivative as defined above (DMCBSu).

However, it should be clearly understood that these examples are given purely for the purposes of illustration of the subject of the invention, of which they do not in any way constitute a limitation.

EXAMPLE 1

Physicochemical Characterizations of the Products Obtained

Acid-base Assay

The acidimetric assay gives an estimation of the number of milliequivalents of carboxymethyl groups and establishes the composition of the final products.

Procedure

A titrating calibration determines the molarity of the sodium hydroxide using a standard: potassium monohydrogen phthalate.

Between 15 and 25 mg of purified, dried (under vacuum at 40° C.) and very accurately weighed product are dissolved in a water/acetone (50/50 v/v) mixture so as to obtain a solution with a final concentration of about 0.25 mg/ml.

The apparent pH, which is then between 7 and 8, is lowered to between 2.8 and 3, using 10% $HNO_3$ solution. The titrating solution is added by means of a precision automatic microburette with a total volume of 5 ml. At least 3 assays are carried out on each product and the results, expressed as milliequivalents of carboxymethyl functions per gram of polymer, make it possible to calculate the degree of substitution with carboxymethyl groups. This method also makes it possible to estimate the degree of substitution with units B, by means of the difference in the number of milliequivalents of carboxymethyl functions before and after benzylamidification. For all of the products, the compositions were established with the aid of elemental analysis.

Nitrogen, Sulfur and Chlorine Elemental Analysis

Assaying the nitrogen and sulfur by elemental analysis, expressed as grams of element per 100 g of product, makes it possible to determine, respectively, the percentage of substitution with benzylamide (B), sulfonate (S) and sulfate (Su) groups.

Assaying the chlorine makes it possible to check the degree of purity of the samples, the percentage of salt (NaCl) not being allowed to exceed 1 to 2% after the purification.

Desulfation of the Products (DCMBSuS)

The product in the form of sodium salt (250 mg, 10 ml) is stirred slowly at room temperature with 3 ml of cation-exchange resin (Amberlite IR120 H$^+$, 16–45 mesh, total exchange capacity: 1.9 meq/ml). After 2 h, the acidic solution is filtered, neutralized with pyridine (1 to 2 ml) to a pH of 6–6.5 and evaporated to dryness. The pyridinium salt obtained is taken up 3 times with 10 ml of anhydrous methanol and evaporated to dryness.

The residue is dispersed in 25 ml of a 90/9/1 mixture of dimethyl sulfoxide (DMSO), methanol and pyridine. The solution is stirred in an oil bath heated at 90° C. for 72 h. The reaction is stopped by adding 20 ml of cold double-distilled water and the mixture is then neutralized with aqueous 1M NaOH solution. The desulfated product is purified by low pressure steric exclusion chromatography on a Sephadex G15 column and then diafiltered on a cell equipped with a membrane with a cutoff threshold of 1000 Da. Between 160 and 210 mg of desulfated product are obtained.

Determination of the Molar Mass

The molar mass of the products prepared is determined by high performance steric exclusion chromatography (HPSEC). Three column systems were used:

- two columns mounted in series (Si300 diol and Hema Sec Bio 40) covering a fractionation range between 106 and 5000 g/mol,
- a Zorbax GF450 column (exclusion range: 450,000–20,000 g/mol),
- a TSK gel G2000 column (exclusion range: 40,000–1000 g/mol).

They are calibrated using a kit of pullulans (853,000 to 5800 g/mol); enzymatic dextran (oligosaccharide, 1500 g/mol); melezitose (trisaccharide, 522 g/mol); sucrose (disaccharide, 342 g/mol) and glucose (monosaccharide, 180 g/mol). The samples to be analyzed are prepared (at 2 mg/mL) and eluted with a solution of 0.15 M NaCl, 0.05 M $Na_2HPO_4$ buffered to pH 7.3. After filtration through a filter of porosity 0.2 μm, 100 μl of the sample are injected, the flow rate being adjusted by means of a Waters model 510 pump and detection at the column outlet being performed by differential refractometry. The chromatograms processed by the GPC Chromstar analysis software make it possible to determine the chromatographic molar mass (Mc), the weight-average molar mass ($\overline{Mp}$) and the number-average molar mass ($\overline{Mn}$) as well as the polydispersity index of the products.

Fourier Transform Infrared Spectroscopy (FTIR)

1 mg of product to be analyzed is mixed with a solution of 150 mg of KBr in 1 ml of double-distilled water. The mixture is filtered through a filter of porosity 0.45 μm, frozen and lyophilized; a disk is prepared with the powder obtained and the spectrum is recorded immediately. The apparatus is an FTIR spectrophotometer (Perkin Elmer model 1600) and the spectra are processed on computer with the IRDM software (Perkin Elmer).

EXAMPLE 2

Preparation of Various DMCBSu's With b= or b≠0

Table I below shows the various derivatives obtained and their properties, established after analysis of the final product.

TABLE I

| Product | Synthesis conditions | Composition Degree of substitution ± 10% | | | Molar mass (g/mol) | Major biological property |
|---|---|---|---|---|---|---|
| | | MC | B | Su | | |
| DMCBSu1 | a | 0.75 | 0.20 | 0.15 | 48,000 | SP |
| DMCBSu2 | b | 0.80 | 0.25 | 0.15 | 70,000 | SP |
| DMCBSu3 | c | 1.10 | 0.40 | 0.40 | 59,000 | C |
| DMCBSu4 | d | 0.70 | 0.30 | 0.25 | 48,000 | SP |

TABLE I-continued

| Product | Synthesis conditions | Composition Degree of substitution ± 10% | | | Molar mass (g/mol) | Major biological property |
|---|---|---|---|---|---|---|
| | | MC | B | Su | | |
| DMCBSu5 | e | 0.80 | 0.35 | 0.15 | 56,000 | PM |
| DMCBSu6 | f | 0.60 | 0.50 | 0.30 | 63,000 | PM |
| DMCBSu7 | g | 0.70 | 0.30 | 0.16 | 70,000 | PM |
| DMCBSu8 | h | 0.70 | 0.20 | 0.35 | 67,000 | SP |
| DMCSu | i | 1.00 | 0 | 0.37 | 70,000 | AC |

SP = substitute for plasma, C = cicatrizing agent, AC = anticoagulant, PM = cell proliferation modulator.

a) DMCBSu1

Carboxymethylation 50 g (0.31 mol) of dextran T40 with a molar mass of about 40,000 is dispersed in 612 ml of isopropanol in a jacketed 2 l reactor maintained at room temperature and fitted with a stirring system.

67.9 g (1.7 mol) of NaOH are dissolved in 188 ml of double-distilled water in a 500 ml beaker. The solution obtained is cooled to 4° C. and added slowly to the dextran-isopropanol mixture. This mixture is stirred for 1 hour.

72.9 g (0.77 mol) of monochloroacetic acid are dissolved in 450 ml of isopropanol (acid/OH molar ratio=2.5) in a 1 l beaker.

The monochloroacetic acid solution is introduced rapidly into the jacketed reactor and the mixture is brought to 60° C. with the aid of a thermostat connected to the reactor. The mixture is maintained at this temperature, with stirring, for 1 h 30 min.

The aqueous phase is then recovered and diluted until a volume of 2.1 l is obtained. The solution thus obtained is purified to constant volume on a membrane with a cutoff threshold of 5000 g/mol, with double-distilled water, until the conductivity of the filtrate is satisfactory. The concentration of the solution is 28 g/l. 20 ml of this solution are frozen and lyophilized for the analyses.

70 g (0.289 mol) of DMC with a degree of substitution with MC of 1.0±0.1 are obtained.

Benzylamidation

The pH of the above solution is adjusted to 4.75. The mixture is cooled to 4° C. 62.3 g of coupling agent (CMC) are added rapidly thereto (CMC/CM molar ratio=0.5). Once the coupling agent is fully dissolved in the mixture, 16 ml of benzylamine are added rapidly (benzylamine/CM molar ratio=0.5). The mixture is then stirred for 16 hours at room temperature.

The mixture is then ultrafiltered to constant volume on a membrane with a cutoff threshold of 5000 g/mol, successively with 15 l of osmosed water to pH 7, then with 10 l of 0.05 M, pH 9.6 carbonate buffer and finally with double-distilled water until the conductivity of the filtrate is satisfactory. The concentration of this solution is 21 g/l (3 l). 20 ml of this concentrated solution are frozen and lyophilized for the analyses. The degrees of substitution with MC and B are, respectively, 0.79±0.07 and 0.22±0.03.

Sulfation

Sulfation requires the preparation of the triethylammonium salt of DMCB.

The solution obtained above is eluted through a column of IR 120 $H^+$ cation-exchange resin (1.5 l). The solution thus acidified is neutralized with triethylamine to a pH close to 7.0.

The neutralized solution is concentrated and lyophilized. About 65 g of triethylammonium salt are obtained.

The 65 g (0.39 mol of free OH) of salt obtained are dried in an oven under vacuum at 40° C. for 5 h, along with any required materials. This salt is then dissolved, in a three-necked round-bottomed flask fitted with a stirring system and an argon circulation system, in 1.7 l of DMSO predried over 4 Å molecular sieves. 24.5 g (0.154 mol) (complex/free OH molar ratio=0.4) of $SO_3$-pyridine complex are dissolved in 300 ml of DMSO and added slowly to the solution of triethylammonium salt of DMCB. The mixture is stirred for 2 h at room temperature under argon.

The reaction is stopped by adding 2 l of double-distilled water at 4° C. to the mixture and the pH of the medium is brought to 7.5–8 using 2 M NaOH solution. The solution is then diluted until a DMSO concentration of 0.5% by volume is obtained, and ultrafiltered to constant volume with double-distilled water on a membrane with a cutoff threshold of 5000 g/mol. The solution is then concentrated to a volume of 5 l and ultrafiltered to constant volume on the same membrane, successively with 10 l of 0.05 M, pH 9.6 carbonate buffer and with double-distilled water until the conductivity of the filtrate is satisfactory. The solution thus purified is concentrated to one-seventh of its volume, frozen and lyophilized. 60 g of DMCBSu1 are thus obtained. The elemental analysis of the sulfur gives a ds with sulfate groups of 0.15±0.02.

b) DMCBSu2

Carboxymethylation 50 g (0.31 mol) of dextran T40 with a molar mass of about 40,000 are dispersed in 612 ml of isopropanol in a 2 l jacketed reactor maintained at room temperature and fitted with a stirring system. 67.9 g (1.7 mol) of NaOH are dissolved in 188 ml in a 500 ml beaker. The solution obtained is cooled to 4° C. and added slowly to the dextran-isopropanol mixture. This mixture is stirred for 1 hour.

87.5 g (0.93 mol) of monochloroacetic acid are dissolved in 450 ml of isopropanol (acid/OH molar ratio =3) in a 1 l beaker.

The monochloroacetic acid solution is introduced rapidly into the jacketed reactor and the mixture is brought to 60° C. with the aid of a thermostat connected to the reactor. The mixture is maintained at this temperature, with stirring, for 2 h.

The aqueous phase is then recovered and diluted until a volume of 2.1 l is obtained. The solution thus obtained is purified to constant volume on a membrane with a cutoff threshold of 5000 g/mol, with double-distilled water, until the conductivity of the filtrate is satisfactory. The concentration of the solution is 28 g/l. 20 ml of this solution are frozen and lyophilized for the analyses.

70 g (0.28 mol) of DMC with a degree of substitution with MC of 1.1±0.1 are obtained.

Benzylamidation

The pH of the above solution is adjusted to 4.75. The mixture is cooled to 4° C. 85.7 g of coupling agent (CMC) are added rapidly thereto (CMC/CM molar ratio=0.7). Once the coupling agent is fully dissolved in the mixture, 22.2 ml of benzylamine are added rapidly (benzylamine/CM molar ratio=0.7). The mixture is then stirred for 16 hours at room temperature.

The mixture is then ultrafiltered to constant volume on a membrane with a cutoff threshold of 5000 g/mol, successively with 15 l of osmosed water to pH 7, then with 10 l of 0.05 M, pH 9.6 carbonate buffer and finally with double-distilled water until the conductivity of the filtrate is satisfactory. The concentration of this solution is 21 g/l (3 l). 20 ml of this concentrated solution are frozen and lyophilized for the analyses. The degrees of substitution with MC and B are, respectively, 0.85±0.07 and 0.27±0.03.

Sulfation

The solution obtained above is eluted through a column of IR 120 H$^+$ cation-exchange resin (1.5 l). The solution thus acidified is neutralized with triethylamine to a pH close to 7.0.

The neutralized solution is concentrated and lyophilized. About 65 g of triethylammonium salt are obtained.

The 65 g (0.365 mol of free OH) of salt obtained are dried in an oven under vacuum at 40° C. for 5 h, along with any required materials. This salt is then dissolved, in a three-necked round-bottomed flask fitted with a stirring system and an argon circulation system, in 1.7 l of DMSO predried over 4 Å molecular sieves. 22.9 g (0.144 mol) (complex/free OH molar ratio=0.4) of $SO_3$-pyridine complex are dissolved in 300 ml of DMSO and added slowly to the polymer solution. The mixture is stirred for 2 h at room temperature under argon.

The reaction is stopped by adding 2 l of double-distilled water at 4° C. to the mixture and the pH of the medium is brought to 7.5–8 using 2 M NaOH solution. The solution is then diluted until a DMSO concentration of 0.5% by volume is obtained, and is ultrafiltered to constant volume with double-distilled water on a membrane with a cutoff threshold of 5000 g/mol. The solution is then concentrated to a volume of 5 l and ultrafiltered to constant volume on the same membrane, successively with 10 l of 0.05 M, pH 9.6 carbonate buffer and with double-distilled water until the conductivity of the filtrate is satisfactory. The solution thus purified is concentrated to one-seventh of its volume, frozen and lyophilized. 60 g of DMCBSu2 with a degree of substitution with Su groups of 0.15±0.02 are thus obtained.

c) DMCBSu3

Carboxymethylation 50 g (0.31 mol) of dextran T40 with a molar mass of about 40,000 are dispersed in 612 ml of isopropanol in a 2 l jacketed reactor maintained at room temperature and fitted with a stirring system.

67.9 g (1.7 mol) of NaOH are dissolved in 188 ml in a 500 ml beaker. The solution obtained is cooled to 4° C. and added slowly to the dextran-isopropanol mixture. This mixture is stirred for 1 hour.

72.9 g (0.77 mol) of monochloroacetic acid are dissolved in 450 ml of isopropanol (acid/OH molar ratio=2.5) in a 1 l beaker.

The monochloroacetic acid solution is introduced rapidly into the jacketed reactor and the mixture is brought to 60° C. with the aid of a thermostat connected to the reactor. The mixture is maintained at this temperature, with stirring, for 2 h.

The aqueous phase is then recovered and purified:
either by means of a double precipitation in 3 l of methanol. The precipitate thus recovered is washed twice with methanol and dried in an oven under vacuum at 40° C.,
or by tangential filtration through a membrane with a cutoff threshold of 5000 daltons.

The purified solution is then concentrated and lyophilized. 70 g (0.289 mol) of DMC with a degree of substitution with MC of 1.0±0.1 are obtained.

Recarboxymethylation of the DMC

The 70 g (0.289 mol or 0.578 mol of free OH) of DMC obtained are dispersed in 1035 ml of isopropanol in a 3 l jacketed reactor maintained at room temperature and fitted with a stirring system.

46.4 g (1.16 mol) of NaOH are dissolved in 265 ml in a 500 ml beaker. The solution obtained is cooled to 4° C. and added slowly to the dextran-isopropanol mixture. This mixture is stirred for 1 hour.

54.6 g (0.578 mol) of monochloroacetic acid are dissolved in 450 ml of isopropanol (acid/free OH molar ratio=1) in a 1 l beaker.

The monochloroacetic acid solution is introduced rapidly into the jacketed reactor and the mixture is brought to 60° C. with the aid of a thermostat connected to the reactor. The mixture is maintained at this temperature, with stirring, for 2 h.

The aqueous phase is then recovered and diluted until a volume of 2.1 l is obtained. The solution thus obtained is purified to constant volume on a membrane with a cutoff threshold of 5000 g/mol, with double-distilled water, until the conductivity of the filtrate is satisfactory. The concentration of the solution is 30 g/l. 20 ml of this solution are frozen and lyophilized for the analyses. 75 g (0.26 mol) of DMC with a degree of substitution with MC of 1.58±0.12 are obtained.

Benzylamidation

The pH of the above solution is adjusted to 4.75. 169 g of coupling agent (CMC) are added rapidly thereto (CMC/CM molar ratio=1). Once the coupling agent is fully dissolved in the mixture, 43.7 ml of benzylamine are added rapidly (benzylamine/CM molar ratio=1). The mixture is then stirred for 16 hours at room temperature.

The mixture is then ultrafiltered to constant volume on a membrane with a cutoff threshold of 5000 g/mol, successively with 15 l of osmosed water to pH 7, then with 10 l of 0.05 M, pH 9.6 carbonate buffer and finally with double-distilled water until the conductivity of the filtrate is satisfactory. The concentration of this solution is 22 g/l (3 l). 20 ml of this solution are frozen and lyophilized for the analyses. The degrees of substitution with MC and B are, respectively, 1.15±0.10 and 0.44±0.04.

Sulfation

The solution obtained above is eluted through a column of IR 120 $H^+$ cation-exchange resin (1.5 l). The solution thus acidified is neutralized with triethylamine to a pH of close to 7.

The neutralized solution is concentrated and lyophilized. About 70 g of triethylammonium salt are obtained.

The 70 g (0.24 mol of free OH) of salt obtained are dried in an oven under vacuum at 40° C. for 5 h, along with any required materials. This salt is then dissolved, in a three-necked round-bottomed flask fitted with a stirring system and an argon circulation system, in 1.7 l of DMSO predried over 4 Å molecular sieves. 30.7 g (0.193 mol) (complex/free OH molar ratio=0.8) of $SO_3$-pyridine complex are dissolved in 300 ml of DMSO and added slowly to the polymer solution. The mixture is stirred for 2 h at room temperature under argon.

The reaction is stopped by adding 2 l of double-distilled water at 4° C. to the mixture and the pH of the medium is brought to 7.5–8 using 2 M NaOH solution. The solution is then diluted until a DMSO concentration of 0.5% by volume is obtained, and is ultrafiltered to constant volume with double-distilled water on a membrane with a cutoff threshold of 5000 g/mol. The solution is then concentrated to a volume of 5 l and ultrafiltered to constant volume on the same membrane, successively with 10 l of 0.05 M, pH 9.6 carbonate buffer and with double-distilled water until the conductivity of the filtrate is satisfactory. The solution thus purified is concentrated to one-seventh of its volume, frozen and lyophilized. 65 g of DMCBSu3 with a degree of substitution with sulfate groups of 0.40±0.04 are thus obtained.

d) DMCBSu4

Carboxymethylation 50 g (0.31 mol) of dextran T40 with a molar mass of about 40,000 are dispersed in 612 ml of isopropanol in a 2 l jacketed reactor maintained at room temperature and fitted with a stirring system.

67.9 g (1.7 mol) of NaOH are dissolved in 188 ml in a 500 ml beaker. The solution obtained is cooled to 4° C. and added slowly to the dextran-isopropanol mixture. This mixture is stirred for 1 hour.

72.9 g (0.77 mol) of monochloroacetic acid are dissolved in 450 ml of isopropanol (acid/OH molar ratio=2.5) in a 1 l beaker.

The monochloroacetic acid solution is introduced rapidly into the jacketed reactor and the mixture is brought to 60° C. with the aid of a thermostat connected to the reactor. The mixture is maintained at this temperature, with stirring, for 2 h.

The aqueous phase is then recovered and diluted until a volume of 2.1 l is obtained. The solution thus obtained is purified to constant volume on a membrane with a cutoff threshold of 5000 g/mol, with double-distilled water, until the conductivity of the filtrate is satisfactory. The concentration of the solution is 28 g/l. 20 ml of this solution are frozen and lyophilized for the analyses.

70 g (0.284 mol) of DMC with a degree of substitution with MC of 1.05±0.10 are obtained.

Benzylamidation

The pH of the above solution is adjusted to 4.75. 126.5 g of coupling agent (CMC) are added rapidly thereto (CMC/CM molar ratio=0.8). Once the coupling agent is fully dissolved in the mixture, 32.6 ml of benzylamine are added rapidly (benzylamine/CM molar ratio=0.8). The mixture is then stirred for 16 hours at room temperature.

The mixture is then ultrafiltered to constant volume on a membrane with a cutoff threshold of 5000 g/mol, successively with 15 l of osmosed water to pH 7, then with 10 l of 0.05 M, pH 9.6 carbonate buffer and finally with double-distilled water until the conductivity of the filtrate is satisfactory. The concentration of this solution is 21 g/l (3 l). 20 ml of this solution are frozen and lyophilized for the analyses. The degrees of substitution with MC and B are, respectively, 0.74±0.06 and 0.33±0.03.

Sulfation

The solution obtained above is eluted through a column of IR 120 $H^+$ cation-exchange resin (1.5 l). The solution thus acidified is neutralized with triethylamine to a pH close to 7.0.

The neutralized solution is concentrated and lyophilized. About 65 g of triethylammonium salt are obtained.

The 65 g (0.38 mol of free OH) of salt obtained are dried in an oven under vacuum at 40° C. for 5 h, along with any required materials. This salt is then dissolved, in a three-necked round-bottomed flask fitted with a stirring system and an argon circulation system, in 1.7 l of DMSO predried over 4 Å molecular sieves. 30.2 g (0.154 mol) (complex/free OH molar ratio=0.5) of $SO_3$-pyridine complex are dissolved in 300 ml of DMSO and added slowly to the polymer solution. The mixture is stirred for 2 h at room temperature under argon.

The reaction is stopped by adding 2 l of double-distilled water at 4° C. to the mixture and the pH of the medium is brought to 7.5–8 using 2 M NaOH solution. The solution is then diluted until a DMSO concentration of 0.5% by volume is obtained, and is ultrafiltered to constant volume with double-distilled water on a membrane with a cutoff threshold of 5000 g/mol. The solution is then concentrated to a volume of 5 l and ultrafiltered to constant volume on the same membrane, successively with 10 l of 0.05 M, pH 9.6 carbonate buffer and with double-distilled water until the conductivity of the filtrate is satisfactory. The solution thus purified is concentrated to one-seventh of its volume, frozen and lyophilized. 60 g of DMCBSu4 with a degree of substitution with Su groups of 0.25±0.03 are thus obtained.

e) DMCBSu5

Carboxymethylation 50 g (0.31 mol) of dextran T40 with a molar mass of about 40,000 are dispersed in 612 ml of isopropanol in a 2 l jacketed reactor maintained at room temperature and fitted with a stirring system.

67.9 g (1.7 mol) of NaOH are dissolved in 188 ml in a 500 ml beaker. The solution obtained is cooled to 4° C. and added slowly to the dextran-isopropanol mixture. This mixture is stirred for 5 l hour.

117.2 g (1.24 mol) of monochloroacetic acid are dissolved in 450 ml of isopropanol (acid/OH molar ratio=4) in a 1 l beaker.

The monochloroacetic acid solution is introduced rapidly into the jacketed reactor and the mixture is brought to 60° C. with the aid of a thermostat connected to the reactor. The mixture is maintained at this temperature, with stirring, for 2 h.

The aqueous phase is then recovered and diluted until a volume of 2.1 l is obtained. The solution thus obtained is purified to constant volume on a membrane with a cutoff threshold of 5000 g/mol, with double-distilled water, until the conductivity of the filtrate is satisfactory. The concentration of the solution is 28 g/l. 20 ml of this solution are frozen and lyophilized for the analyses.

70 g (0.271 mol) of DMC with a degree of substitution with MC of 1.2±0.11 are obtained.

Benzylamidation

The pH of the above solution is adjusted to 4.75. 124.1 g of coupling agent (CMC) are added rapidly thereto (CMC/CM molar ratio=0.9). Once the coupling agent is fully dissolved in the mixture, 35.5 ml of benzylamine are added rapidly (benzylamine/CM molar ratio=0.9). The mixture is then stirred for 16 hours at room temperature.

The mixture is then ultrafiltered to constant volume on a membrane with a cutoff threshold of 5000 g/mol, successively with 15 l of osmosed water to 35 pH 7, then with 10 l of 0.05 M, pH 9.6 carbonate buffer and finally with double-distilled water until the conductivity of the filtrate is satisfactory. The concentration of this solution is 21 g/l (3 l). 20 ml of this solution are frozen and lyophilized for the analyses. The degrees of substitution with MC and B are, respectively, 0.84±0.07 and 0.38±0.04.

Sulfation

The solution obtained above is eluted through a column of IR 120 H$^+$ cation-exchange resin (1.5 l). The solution thus acidified is neutralized with triethylamine to a pH close to 7.

The neutralized solution is concentrated and lyophilized. About 67 g of triethylammonium salt are obtained.

The 67 g (0.33 mol of free OH) of salt obtained are dried in an oven under vacuum at 40° C. for 5 h, along with any required materials. This salt is then dissolved, in a three-necked round-bottomed flask fitted with a stirring system and an argon circulation system, in 1.7 l of DMSO predried over 4 Å molecular sieves. 21 g (0.132 mol) (complex/free OH molar ratio=0.4) of $SO_3$-pyridine complex are dissolved in 300 ml of DMSO and added slowly to the polymer solution. The mixture is stirred for 2 h at room temperature under argon.

The reaction is stopped by adding 2 l of double-distilled water at 4° C. to the mixture and the pH of the medium is brought to 7.5–8 using 2 M NaOH solution. The solution is then diluted until a DMSO concentration of 0.5% by volume is obtained, and is ultrafiltered to constant volume with double-distilled water on a membrane with a cutoff threshold of 5000 g/mol. The solution is then concentrated to a volume of 5 l and ultrafiltered to constant volume on the same membrane, successively with 10 l of 0.05 M, pH 9.6 carbonate buffer and with double-distilled water until the conductivity of the filtrate is satisfactory. The solution thus purified is concentrated to one-seventh of its volume, frozen and lyophilized. 62 g of DMCBSu5 with a degree of substitution with sulfate groups of 0.15±0.02 are thus obtained.

f) DMCBSu6

Carboxymethylation 50 g (0.31 mol) of dextran T40 with a molar mass of about 40,000 are dispersed in 612 ml of isopropanol in a 2 l jacketed reactor maintained at room temperature and fitted with a stirring system.

67.9 g (1.7 mol) of NaOH are dissolved in 188 ml in a 500 ml beaker. The solution obtained is cooled to 4° C. and added slowly to the dextran-isopropanol mixture. This mixture is stirred for 1 hour.

87.5 g (0.93 mol) of monochloroacetic acid are dissolved in 450 ml of isopropanol (acid/OH molar ratio 3) in a 1 l beaker.

The monochloroacetic acid solution is introduced rapidly into the jacketed reactor and the mixture is brought to 60° C. with the aid of a thermostat connected to the reactor. The mixture is maintained at this temperature, with stirring, for 2 h.

The aqueous phase is then recovered and diluted until a volume of 2.1 l is obtained. The solution thus obtained is purified to constant volume on a membrane with a cutoff threshold of 5000 g/mol, with double-distilled water, until the conductivity of the filtrate is satisfactory. The concentration of the solution is 28 g/l. 20 ml of this solution are frozen and lyophilized for the analyses.

70 g (0.28 mol) of DMC with a degree of substitution with MC of 1.1±0.10 are obtained.

1st benzylamidation

The pH of the above solution is adjusted to 4.75. 130.5 g of coupling agent (CMC) are added rapidly thereto (CMC/CM molar ratio=1). Once the coupling agent is fully dissolved in the mixture, 30.3 ml of benzylamine are added rapidly (benzylamine/CM molar ratio=0.9). The mixture is then stirred for 16 hours at room temperature.

The mixture is then ultrafiltered to constant volume on a membrane with a cutoff threshold of 5000 g/mol, successively with 15 l of osmosed water to pH 7, then with 10 l of 0.05 M, pH 9.6 carbonate buffer and finally with double-distilled water until the conductivity of the filtrate is satisfactory. The solution is concentrated to a volume of 2.1 l (~28 g/l or 0.1 mol/l). 20 ml of this solution are frozen and lyophilized for the analyses. The degrees of substitution with MC and B are, respectively, 0.75±0.06 and 0.38±0.04.

2nd benzylamidation

The pH of the 2.1 l of the above DMCB solution is readjusted to 4.75. The mixture is cooled to 4° C. 40 g of coupling agent (CMC) are added rapidly thereto (CMC/CM molar ratio=0.5). Once the coupling agent is fully dissolved in the mixture, 10.3 ml of benzylamine are added rapidly (benzylamine/CM molar ratio=0.5). The mixture is then stirred for 16 hours at room temperature.

The mixture is then ultrafiltered to constant volume on a membrane with a cutoff threshold of 5000 g/mol, successively with 15 l of osmosed water to pH 7, then with 10 l of 0.05 M, pH 9.6 carbonate buffer and finally with double-distilled water until the conductivity of the filtrate is satisfactory. The concentration of this solution is 21 g/l (3 l). 20 ml of this solution are frozen and lyophilized for the analyses. The degrees of substitution with MC and B are, respectively, 0.65±0.06 and 0.54±0.05.

Sulfation

The solution obtained above is eluted through a column of IR 120 H$^+$ cation-exchange resin (1.5 l). The solution thus acidified is neutralized with triethylamine to a pH close to 7.

The neutralized solution is concentrated and lyophilized. About 65 g of triethylammonium salt are obtained.

The 65 g (0.365 mol of free OH) of salt obtained are dried in an oven under vacuum at 40° C. for 5 h, along with any required materials. This salt is then dissolved, in a three-necked round-bottomed flask fitted with a stirring system and an argon circulation system, in 1.7 l of DMSO predried over 4 Å molecular sieves. 34.9 g (0.219 mol) (complex/free OH molar ratio=0.6) of $SO_3$-pyridine complex are dissolved in 300 ml of DMSO and added slowly to the polymer solution. The mixture is stirred for 2 h at room temperature under argon.

The reaction is stopped by adding 2 l of double-distilled water at 4° C. to the mixture and the pH of the medium is brought to 7.5–8 using 2 M NaOH solution. The solution is then diluted until a DMSO concentration of 0.5% by volume is obtained, and is ultrafiltered to constant volume with double-distilled water on a membrane with a cutoff threshold of 5000 g/mol. The solution is then concentrated to a volume of 5 l and ultrafiltered to constant volume on the same membrane, successively with 10 l of 0.05 M, pH 9.6 carbonate buffer and with double-distilled water until the conductivity of the filtrate is satisfactory. The solution thus purified is concentrated to one-seventh of its volume, frozen and lyophilized. 60 g of DMCBSu6 with a degree of substitution with sulfate groups of 0.30±0.03 are thus obtained.

g) DMCBSu7

Carboxymethylation 50 g (0.31 mol) of dextran T40 with a molar mass of about 40,000 are dispersed in 612 ml of isopropanol in a 2 l jacketed reactor maintained at room temperature and fitted with a stirring system.

67.9 g (1.7 mol) of NaOH are dissolved in 188 ml in a 500 ml beaker. The solution obtained is cooled to 4° C. and added slowly to the dextran-isopropanol mixture. This mixture is stirred for 1 hour.

72.9 g (0.77 mol) of monochloroacetic acid are dissolved in 450 ml of isopropanol (acid/OH molar ratio=2.5) in a 1 l beaker.

The monochloroacetic acid solution is introduced rapidly into the jacketed reactor and the mixture is brought to 60° C. with the aid of a thermostat connected to the reactor. The mixture is maintained at this temperature, with stirring, for 2 h.

The aqueous phase is then recovered and diluted until a volume of 2.1 l is obtained. The solution thus obtained is purified to constant volume on a membrane with a cutoff threshold of 5000 g/mol, with double-distilled water, until the conductivity of the filtrate is satisfactory. The concentration of the solution is 28 g/l. 20 ml of this solution are frozen and lyophilized for the analyses.

70 g (0.284 mol) of DMC with a degree of substitution with MC of 1.05 are obtained.

Benzylamidation

The pH of the above solution is adjusted to 4.75. 126.5 g of coupling agent (CMC) are added rapidly thereto (CMC/CM molar ratio=0.8). Once the coupling agent is fully dissolved in the mixture, 32.6 ml of benzylamine are added rapidly (benzylamine/CM molar ratio=0.8). The mixture is then stirred for 16 hours at room temperature.

The mixture is then ultrafiltered to constant volume on a membrane with a cutoff threshold of 5000 g/mol, successively with 15 l of osmosed water to pH 7, then with 10 l of 0.05 M, pH 9.6 carbonate buffer and finally with double-distilled water until the conductivity of the filtrate is satisfactory. The concentration of this solution is 21 g/l (3 l). 20 ml of this solution are frozen and lyophilized for the analyses. The degrees of substitution with MC and B are, respectively, 0.74±0.06 and 0.33±0.03.

Sulfation

The solution obtained above is eluted through a column of IR 120 H$^+$ cation-exchange resin (1.5 l). The solution thus acidified is neutralized with triethylamine to a pH close to 7.

The neutralized solution is concentrated and lyophilized. About 65 g of triethylammonium salt are obtained.

The 65 g (0.38 mol of free OH) of salt obtained are dried in an oven under vacuum at 40° C. for 5 h, along with any required materials. This salt is then dissolved, in a three-necked round-bottomed flask fitted with a stirring system and an argon circulation system, in 1.7 l of DMSO predried over 4 Å molecular sieves. 24.2 g (0.154 mol) (complex/free OH molar ratio=0.4) of $SO_3$-pyridine complex are dissolved in 300 ml of DMSO and added slowly to the polymer solution. The mixture is stirred for 2 h at room temperature under argon.

The reaction is stopped by adding 2 l of double-distilled water at 4° C. to the mixture and the pH of the medium is brought to 7.5–8 using 2 M NaOH solution. The solution is then diluted until a DMSO concentration of 0.5% by volume is obtained, and is ultrafiltered to constant volume with double-distilled water on a membrane with a cutoff threshold of 5000 g/mol. The solution is then concentrated to a volume of 5 l and ultrafiltered to constant volume on the same membrane, successively with 10 l of 0.05 M, pH 9.6 carbonate buffer and with double-distilled water until the conductivity of the filtrate is satisfactory. The solution thus purified is concentrated to one-seventh of its volume, frozen and lyophilized. 60 g of DMCBSu7 with a degree of substitution with sulfate groups of 0.16±0.02 are thus obtained.

h) DMCBSu8

Carboxymethylation 50 g (0.31 mol) of dextran T40 with a molar mass of about 40,000 are dispersed in 612 ml of isopropanol in a 2 l jacketed reactor maintained at room temperature and fitted with a stirring system. 67.9 g (1.7 mol) of NaOH are dissolved in 188 ml in a 500 ml beaker. The solution obtained is cooled to 4° C. and added slowly to the dextran-isopropanol mixture. This mixture is stirred for 1 hour.

72.9 g (0.77 mol) of monochloroacetic acid are dissolved in 450 ml of isopropanol (acid/OH molar ratio=2.5) in a 1 l beaker.

The monochloroacetic acid solution is introduced rapidly into the jacketed reactor and the mixture is brought to 60° C. with the aid of a thermostat connected to the reactor. The mixture is maintained at this temperature, with stirring, for 2 h.

The aqueous phase is then recovered and diluted until a volume of 2.1 l is obtained. The solution thus obtained is purified to constant volume on a membrane with a cutoff threshold of 5000 g/mol, with double-distilled water, until the conductivity of the filtrate is satisfactory. The concentration of the solution is 28 g/l. 20 ml of this solution are frozen and lyophilized for the analyses.

70 g (0.295 mol) of DMC with a degree of substitution with MC of 0.94±0.10 are obtained.

Benzylamidation

The pH of the above solution is adjusted to 4.75. The mixture is cooled to 4° C. 58.8 g of coupling agent (CMC) are added rapidly thereto (CMC/CM molar ratio=0.5). Once the coupling agent is fully dissolved in the mixture, 15.2 ml of benzylamine are added rapidly (benzylamine/CM molar ratio=0.5). The mixture is then stirred for 16 hours at room temperature.

The mixture is then ultrafiltered to constant volume on a membrane with a cutoff threshold of 5000 g/mol, successively with 15 l of osmosed water to pH 7, then with 10 l of 0.05 M, pH 9.6 carbonate buffer and finally with double-distilled water until the conductivity of the filtrate is satisfactory. The concentration of this solution is 21 g/l (3 l). 5 ml of this solution are frozen and lyophilized for the analyses. The degrees of substitution with MC and B are, respectively, 0.75±0.07 and 0.22±0.03.

Sulfation

The solution obtained above is eluted through a column of IR 120 H$^+$ cation-exchange resin (1.5 l). The solution thus acidified is neutralized with triethylamine to a pH close to 7.

The neutralized solution is concentrated and lyophilized. About 65 g of triethylammonium salt are obtained.

The 65 g (0.4 mol of free OH) of salt obtained are dried in an oven under vacuum at 40° C. for 5 h, along with any required materials. This salt is then dissolved, in a three-necked round-bottomed flask fitted with a stirring system and an argon circulation system, in 1.7 l of DMSO predried over 4 Å molecular sieves. 45.2 g (0.154 mol) (complex/free OH molar ratio=0.7) of $SO_3$-pyridine complex are dissolved in 300 ml of DMSO and added slowly to the polymer solution. The mixture is stirred for 2 h at room temperature under argon.

The reaction is stopped by adding 2 l of double-distilled water at 4° C. to the mixture and the pH of the medium is brought to 7.5–8 using 2 M NaOH solution. The solution is then diluted until a DMSO concentration of 0.5% by volume is obtained, and is ultrafiltered to constant volume with double-distilled water on a membrane with a cutoff threshold of 5000 g/mol. The solution is then concentrated to a volume of 5 l and ultrafiltered to constant volume on the same membrane, successively with 10 l of 0.05 M, pH 9.6 carbonate buffer and with double-distilled water until the conductivity of the filtrate is satisfactory. The solution thus purified is concentrated to one-seventh of its volume, frozen and lyophilized. 60 g of DMCBSu8 with a degree of substitution with sulfate groups of 0.35±0.04 are thus obtained.

i) DMCSu

Carboxymethylation 50 g (0.31 mol) of dextran T40 with a molar mass of about 40,000 are dispersed in 612 ml of isopropanol in a 2 l jacketed reactor maintained at room temperature and fitted with a stirring system.

67.9 g (1.7 mol) of NaOH are dissolved in 188 ml in a 500 ml beaker. The solution obtained is cooled to 4° C. and added slowly to the dextran-isopropanol mixture. This mixture is stirred for 1 hour.

72.9 g (0.77 mol) of monochloroacetic acid are dissolved in 450 ml of isopropanol (acid/OH molar ratio=2.5) in a 1 l beaker.

The monochloroacetic acid solution is introduced rapidly into the jacketed reactor and the mixture is brought to 60° C. with the aid of a thermostat connected to the reactor. The mixture is maintained at this temperature, with stirring, for 2 h.

The aqueous phase is then recovered and diluted until a volume of 2.1 l is obtained. The solution thus obtained is purified to constant volume on a membrane with a cutoff threshold of 5000 g/mol, with double-distilled water, until the conductivity of the filtrate is satisfactory. The concentration of the solution is 28 g/l. 20 ml of this solution are frozen and lyophilized for the analyses.

70 g (0.289 mol) of DMC with a degree of substitution with MC of 1.0±0.1 are obtained.

Sulfation

The solution obtained above is eluted through a column of IR 120 H$^+$ cation-exchange resin (1.5 l). The solution thus acidified is neutralized with triethylamine to a pH close to 7.

The neutralized solution is concentrated and lyophilized. About 80 g of triethylammonium salt are obtained.

The 80 g (0.466 mol of free OH) of salt obtained are dried in an oven under vacuum at 40° C. for 5 h, along with any required materials. This salt is then dissolved, in a three-necked round-bottomed flask fitted with a stirring system and an argon circulation system, in 1.7 l of DMSO predried over 4 Å molecular sieves. 52 g (0.326 mol) (complex/free OH molar ratio=0.7) of $SO_3$-pyridine complex are dissolved in 300 ml of DMSO and added slowly to the polymer solution. The mixture is stirred for 2 h at room temperature under argon.

The reaction is stopped by adding 2 l of double-distilled water at 4° C. to the mixture and the pH of the medium is brought to 7.5–8 using 2 M NaOH solution. The solution is then diluted until a DMSO concentration of 0.5% by volume is obtained, and is ultrafiltered to constant volume with double-distilled water on a membrane with a cutoff threshold of 5000 g/mol. The solution is then concentrated to a volume of 5 l and ultrafiltered to constant volume on the same membrane, successively with 10 l of 0.05 M, pH 9.6 carbonate buffer and with double-distilled water until the conductivity of the filtrate is satisfactory. The solution thus purified is concentrated to one-seventh of its volume, frozen and lyophilized. 70 g of DMCSu are thus obtained. Elemental analysis of the sulfur gives a ds with sulfate groups of 0.37±0.04.

EXAMPLE 3

Preparation of a DMCBSuS

A suspension of 10 9 of DMCBSu, obtained in accordance with Example 2, in 350 ml of anhydrous dichloromethane is prepared. 0.62 ml of chlorosulfonic acid is added to 35 ml of anhydrous dichloromethane (chlorosulfonic acid/units B molar ratio=1). The mixture is stirred under argon for 1 hour at room temperature. The product is filtered through a No. 4 sinter funnel and washed successively with 200 ml of dichloromethane, 200 ml of 50/50 (v/v) dichloromethane/dioxane and finally with pure dioxane.

The DMCBSuS in acid form is immediately dissolved in 150 ml of water and the pH of the solution is adjusted to 9 with 6 M NaOH and maintained at this value for 1 hour. The solution is then neutralized with 0.1 M HCl, frozen and lyophilized.

The amount of sulfonates is established by the difference between the sulfur contents of the initial and final products after desulfation of the two products, under the conditions specified in Example 1.

EXAMPLE 4

Process Variant for the Preparation of a DMCBSu.

a) Preparation of the Reagent N-methylphenyl-2-chloroacetamide 109.4 ml (1 mol) of benzylamine are mixed with 1 l of ether predried over 4 Å molecular sieves, in a three-necked round-bottomed flask fitted with a stirring system and an argon circulation system (inert atmosphere).

79.7 ml (1 mol) of chloroacetyl chloride are added dropwise (introduction time of 30 minutes), using a dropping funnel. After the addition, the flask is sealed and stirred at room temperature for 1 hour.

The mixture is then washed successively with 1.5 l of 0.5 M citric acid solution (220 g), 1.5 l of double-distilled water at 4° C., 1.5 l of 0.5 M sodium hydrogen carbonate solution (63 g) and 1.5 l of 1 M NaCl solution (87.8 g).

The ether phase is recovered and evaporated to dryness.

The dry residue is purified by double-recrystallization from water:

the residue is dissolved in double-distilled water (1–2 w/v% solution) brought to the boiling point. This boiling solution is filtered using a No. 4 sinter funnel preheated to 100° C. The filtered solution is cooled and stored at 4° C. overnight. The reagent is then recovered on Wattman paper and dried in an oven under vacuum at about 50° C.

b) Synthesis of DMCB 50 g (0.31 mol) of dextran T40 with a molar mass of about 40,000 are dispersed in 400 ml of isopropanol in a 2 l jacketed reactor fitted with a stirring system.

56.5 g (1.41 mol) of NaOH are dissolved in 225 ml in a 500 ml beaker. The solution obtained is cooled to 4° C. and added slowly to the dextran-isopropanol mixture. The mixture is stirred for 1 hour. 84.9 g (0.46 mol) of the N-methylphenyl-2-chloroacetamide obtained in a) are dissolved in 675 ml of isopropanol in a 1 l beaker. 43.7 g (0.46 mol) of monochloroacetic acid are dissolved in 200 ml of isopropanol in another, 500 ml beaker.

The N-methylphenyl-2-chloroacetamide solution is introduced rapidly into the jacketed reactor and the mixture is brought to 60° C. with the aid of a thermostat connected to the reactor. About 5 minutes later, the monochloroacetic acid solution is rapidly added thereto and the mixture is stirred at 60° C. for 2 hours.

The aqueous phase is then recovered and purified:

either by means of a double precipitation in 3 l of methanol; the precipitate thus recovered is washed twice with methanol and dried in an oven under vacuum at 40° C., or by tangential filtration through a membrane with a cutoff threshold of 5000 daltons; the purified solution is then concentrated and lyophilized.

The composition of the DMC obtained by this method is as follows: MC=0.90±0.09 and B=0.30±0.03.

c) Synthesis of DMCBSu

Formation of the Tributylammonium (or Triethylammonium) Salt 50 g (0.18 mol) of the DMCB obtained in step b) are dissolved in 2 l of double-distilled water. The solution obtained is eluted through a column of cation-exchange resin (Amberlite IR 120 H$^+$). The product thus acidified is neutralized with 10% tributylamine in ethanol (or triethylamine) to a pH close to 7.

The neutralized solution is purified by tangential filtration through a membrane with a cutoff threshold of 5000 daltons, concentrated and lyophilized. About 60 g of tributylammonium (or triethylammonium) salt are obtained.

Sulfation of the Tributylammonium (or Trithylammonium) DMCB

The 60 g of salt obtained are dried in an oven under vacuum at 40° C. for 4 hours, along with any materials required. The salt is then dissolved in a three-necked round-bottomed flask fitted with a stirring system and an argon circulation system, in 2.7 l of N,N-dimethylformamide (DMF) predried over 4 Å molecular sieves (5.7 l for the triethylammonium salt). 38.7 g (0.24 mol) of SO$_3$-pyridine complex (46.6 g (0.29 mol) in the case of the triethylammonium salt) are dissolved in 300 ml of DMF and added slowly to the polymer solution. The mixture is stirred for 2 hours at room temperature.

The reaction is stopped by adding 3 l of double-distilled water at 4° C. to the mixture and the pH of the medium is brought to 7.5–8 using 2 M NaOH solution. The solution is then ultrafiltered through a membrane with a cutoff threshold of 5000 daltons, concentrated and lyophilized.

EXAMPLE 5

Synthesis of DMCSu a) Synthesis of DMC 50 g (0.31 mol) of dextran T40 with a molar mass of about 40,000 are dispersed in 612 ml of isopropanol in a 2 l jacketed reactor fitted with a stirring system.

67.9 g (1.7 mol) of NaOH are dissolved in 188 ml in a 500 ml beaker. The solution obtained is cooled to 4° C. and added slowly to the dextran-isopropanol mixture. This mixture is stirred for 1 hour.

72.9 g (0.77 mol) of monochloroacetic acid are dissolved in 450 ml of isopropanol in a 1 l beaker.

The monochloroacetic acid solution is introduced rapidly into the jacketed reactor and the mixture is brought to 60° C. with the aid of a thermostat connected to the reactor. The mixture is maintained at this temperature, with stirring, for 2 hours.

The aqueous phase is then recovered and purified:

either by means of a double precipitation in 3 l of methanol; the precipitate thus recovered is washed twice with methanol and dried in an oven under vacuum at 40° C., or by tangential filtration through a membrane with a cutoff threshold of 5000 daltons; the purified solution is then concentrated and lyophilized.

b) Synthesis of DMCSu

Formation of the Tributylammonium (or Triethylammonium) Salt 50 g (0.18 mol) of DMC are dissolved in 2 l of double-distilled water. The solution obtained is eluted through a column of cation-exchange resin (Amberlite IR 120 H$^+$). The product thus acidified is neutralized with 10% tributylammonium [sic] in ethanol (or triethylamine) to a pH close to 7.

The neutralized solution is purified by tangential filtration through a membrane with a cutoff threshold of 5000 daltons, concentrated and lyophilized. About 60 g of tributylammonium (or triethylammonium) salt are obtained.

Sulfation of Tributylammonium (or Triethylammonium) DMC

The 60 g of salt obtained are dried in an oven under vacuum at 40° C. for 4 hours, along with any required materials. The salt is then dissolved, in a three-necked round-bottomed flask fitted with a stirring system and an argon circulation system, in 2.7 l of N,N-dimethylformamide (DMF) predried over 4 Å molecular sieves. 44.8 g (0.28 mol) of SO$_3$-pyridine complex (or 55.8 g (0.35 mol) in the case of the triethylammonium salt) are dissolved in 300 ml of DMF and added slowly to the polymer solution. The mixture is stirred for 2 hours at room temperature under argon.

The reaction is stopped by adding 3 l of double-distilled water at 4° C. to the mixture and the pH of the medium is brought to 7.5–8 using 2 M NaOH solution. The solution is then ultrafiltered through a membrane with a cutoff threshold of 5000 daltons, concentrated and lyophilized.

The composition of a DMCSu obtained is as follows: MC=1±0.1, Su=0.37±0.04.

EXAMPLE 6

Synthesis of a DBSu a) Synthesis of DB 50 g (0.31 mol) of dextran T40 with a molar mass of about 40,000 are dispersed in 400 ml of isopropanol in a 2 l jacketed reactor fitted with a stirring system.

56.5 g (1.41 mol) of NaOH are dissolved in 225 ml in a 500 ml beaker. The solution obtained is cooled to 4° C. and added slowly to the dextranisopropanol mixture. This mixture is stirred for 1 hour.

84.9 g (0.46 mol) of N-methylphenyl-2-chloroacetamide (see Example 5) are dissolved in 875 ml of isopropanol in a 1 l beaker. The solution obtained is introduced rapidly into the jacketed reactor and the mixture is brought to 60° C. with the aid of a thermostat connected to the reactor; the mixture is maintained at this temperature, with stirring, for 2 hours.

The aqueous phase is then recovered and purified:

either by means of a double precipitation in 3 l of methanol; the precipitate thus recovered is washed twice with methanol and dried in an oven under vacuum at 40° C.;

or by tangential filtration through a membrane with a cutoff threshold of 5000 daltons; the purified solution is then concentrated and lyophilized.

About 60 g of DB are obtained. The composition of the product is as follows: B=0.3±0.003.

b) Synthesis of DBSu

The 60 g of DB obtained are dried in an oven under vacuum at 40° C. for 4 hours, along with any materials required. The product is then dispersed, in a three-necked round-bottomed flask fitted with a stirring system and an argon circulation system, in 2.7 l of N,N-dimethylformamide (DMF) predried over 4 Å molecular sieves. 40.7 g (0.26 mol) of $SO_3$-pyridine complex are dissolved in 300 ml of DMF and added slowly to the polymer solution. The mixture is stirred for 2 hours at room temperature under argon.

The reaction is stopped by adding 3 l of double-distilled water at 4° C. to the mixture and the pH of the medium is brought to 7.5–8 using 2 M NaOH solution. The solution is then ultrafiltered through a membrane with a cutoff threshold of 5000 daltons, concentrated and lyophilized.

The composition of a DBSu obtained is as follows: B=0.3±0.03 and Su=0.14±0.02.

EXAMPLE 7

Anticoagulant and Anti-complement Activity of the Products According to the Invention a) Measurement of the Anticoagulant Activity The activated cephalin time is an exploratory test which is sensitive to all the factors of the endogenous pathway (thrombin, V, VIII, IX, XI and XII) of the coagulation system except for platelet factor III. The reagent used (APTT, Organon Teknika) contains rabbit brain phospholipids (platelet factor III) and a particulate activator (micronized silica or elagic acid). The procedure used is as follows:

100 $\mu$l of platelet-poor human plasma (PPP)

100 $\mu$l of Owren Koller buffer (OKB)

100 $\mu$l of APTT reagent incubation for 3 min at 37° C.

100 $\mu$l of 25 mM calcium chloride ($CaCl_2$)

measurement of the time for appearance of the clot.

A curve is plotted, of the logarithm of the coagulation time as a function of the polymer concentration. The slope of the curve makes it possible to calculate the specific anticoagulant activity of the polysaccharide according to the equation:

$$a\ (\text{IU/mg}) = \frac{\text{slope of the DMCBSu curve}}{\text{slope of the heparin curve}} \times \frac{\text{specific anticoagulant activity}}{\text{of the heparin standard used}}$$

b) Measurement of the Inhibition of the Activation of Complement

The action of dextran derivatives of variable chemical composition was studied in a hemolytic or CH50 assay, according to a procedure in which the human serum is incubated with one of the dextran derivatives of the invention for 30 minutes at 37° C. before being activated with sheep erythrocytes sensitized with rabbit anti(sheep red blood cells) antibodies (EA). By definition, one CH50 unit corresponds to the concentration of complement proteins (contained in one milliliter of serum) capable of inducing the hemolysis of 50% of $2 \times 10^7$ activated EAs in a reaction medium in which the volume, the temperature and the reaction time are kept constant. The number of hemolytic sites per cell is calculated.

The activity in terms of the inhibition of complement activation is expressed as a percentage of inhibition of the formation of convertase relative to the control tube in which the number of hemolytic sites is determined in the absence of dextran derivative.

This activity, A, is expressed as weight of product (at constant volume) ($\mu$g), required for 50% inhibition of the formation of hemolytic sites. This expression of the anti-complement activity means that it is inversely proportional to the weight of product. In other words, the anti-complement activity is proportionately higher the lower the weight of product.

This activity varies as a function of the overall chemical composition of the product.

The results obtained with 5 derivatives according to the invention are illustrated in Table II below, which recalls their overall chemical composition and their specific anticoagulant activity, a, expressed in international units per mg of product (relative to heparin at 173 IU/mg).

TABLE II

| Sample reference | Chemical composition | | | Anti-complement activity A | Anti-coagulent activity a |
|---|---|---|---|---|---|
| | MC | B | Su | $\mu$g | IU/mg |
| Dextran | 0 | 0 | 0 | 1250 | 0 |
| Dextran MC | 1.0 | 0 | 0 | 570 | 0 |

TABLE II-continued

| Sample reference | Chemical composition | | | Anti-complement activity A | Anti-coagulent activity a |
|---|---|---|---|---|---|
| | MC | B | Su | µg | IU/mg |
| DMCBSu1 | 0.75 | 0.20 | 0.15 | 150 | 0.02 |
| DMCBSu2 | 0.80 | 0.25 | 0.15 | 150 | 0.04 |
| DMCBSu3 | 1.10 | 0.40 | 0.40 | 35 | 4.0 |
| DMCBSu4 | 0.70 | 0.30 | 0.25 | 125 | 0.08 |
| DMCB1 | 0.80 | 0.10 | 0 | 300 | 0 |
| Heparin | — | — | — | 2700 | 173 |

It is found that the anti-complement activity increases as the ds with MC and Su units increases. Above a ds with MC units of about 0.40, the anticoagulant activity increases as the ds with Su units increases.

It is observed that the derivatives with low values of ds with Su units already have high anti-complement activity, whereas their anticoagulant activity is very low. Finally, it is noted that the presence of MC and B units alone induces slight anti-complement activity, whereas it has no anticoagulant effect.

These results show that it is possible to obtain products endowed with high inhibitory activity on the activation of complement and very low specific anticoagulant activity.

EXAMPLE 8

Antiproliferative Activity of the Compounds According to the Invention

The DMCBSu compounds have stimulatory or inhibitory effects on cell growth, depending on the nature of the cells. Thus, for example in the cardiovascular field, the products have the advantage of stimulating the growth of endothelial cells and inhibiting the growth of smooth muscle cells (SMC). These properties are important in pharmacology, their major advantage being the prevention of restenosis after angioplasty or cardiovascular surgical interventions.

The antiproliferative activity of DMCBSu's was studied on smooth muscle cells (SMC) of rat aorta. 24 hours after inoculating the cells in a medium containing 10% fetal calf serum (FCS), the cells are subjected to deficient conditions for 3 days (medium containing 0.1% FCS) (this allows the cells to become synchronized by stopping them at the GO/G1 stage of the cell cycle). The cells are then fed again with medium containing 10% FCS, also containing variable concentrations of the test product (from 0 to 1 mg/ml). A control is prepared under the same conditions but without the addition of product.

After growing them for 5 days, the cells are counted (using an automatic counter or by measuring the radioactivity in counts per minute after incorporating tritiated thymidine) and the inhibition is determined as follows, the abbreviation "nb" denoting the word "number":

%I=(1−(nb of Cells in the Presence of Product)/(nb of Cells Without Product))×100

The anticoagulant activity of the various products was also determined.

Table III below collates the results obtained for two DMCBSu's as well as for native dextran and heparin.

TABLE III

| Product | Composition (ds) | | | Anticoagulant activity | I |
|---|---|---|---|---|---|
| | MC | B | Su | IU/mg | (%) |
| Dextran | 0 | 0 | 0 | 0 | 0 |
| DMCBSu6 | 0.60 | 0.50 | 0.30 | 5.0 | 80 |
| DMCBSu5 | 0.80 | 0.35 | 0.15 | 3.0 | 85 |
| Heparin | | | | 173 | 80 |

These results show that, for DMCBSu6 and DMCBSu5, the inhibition (I) of the cell growth of smooth muscle cells is comparable to, or even greater than, that of heparin. However, these two products have markedly lower anticoagulant activity than that of heparin.

EXAMPLE 9

Potentiation of Cell Growth in the Presence of Fibroblast Growth Factors (FGF)

The proliferative activity of the DMCBSu's was evaluated on 2 cell lines:

CCL39: Chinese hamster lung fibroblast line.

HUCVEC: endothelial cells of the human umbilical cord vein.

The growth tests are carried out by maintaining the cells under deficient conditions, i.e. in a culture medium containing 0% or 2% fetal calf serum, followed by incorporating the test product at different concentrations.

The countings are carried out using an automatic counter or by measuring the radioactivity, in counts per minute, after incorporating tritiated thymidine.

The capacity of the products to potentiate and protect certain growth factors such as FGFs is evaluated according to the following procedure.

The mitogenic activity of the FGFs studied is measured by means of a biological activity test (dose-response test) in order to determine the $ED_{50}$ (amount of growth factor required to obtain half the maximum incorporation of tritiated thymidine into the cells).

This $ED_{50}$ is 5 ng/ml for the CCL39 cells and 2 ng/ml for the HUCVEC cells.

These $ED_{50}$ values are used for the rest of the studies.

For the HUCVEC cells, the combination of FGF (2 ng/ml) with 400 µg/ml of DMCBSu5 has the same mitogenic power as the FGF alone at 20 ng/ml.

For the CCL39 cells, in the absence of DMCBSu, the $ED_{50}$ is about 5 ng/ml of FGF. In the presence of 1000 µg/ml of DMCBSu1, the $ED_{50}$ falls to 0.8 ng/ml.

These results show the potentiating effect of the cell growth factors considered by the DMCBSu's. This effect is linked to the overall chemical composition of the products. The table below gives, for example, the overall chemical composition of particularly active DMCBSu's.

| COMPOSITIONS OF DMCBSU's (in ds) | | | |
|---|---|---|---|
| | MC | B | Su |
| DMCBSu1 | 0.75 | 0.20 | 0.15 |
| DMCBSu5 | 0.80 | 0.35 | 0.15 |
| DMCBSu3 | 1.10 | 0.40 | 0.40 |

As emerges from the preceding account, the invention is not in any way limited to its implementation, preparation or application methods which have just been described in greater detail; on the contrary, it encompasses all the variants which may occur to a person skilled in the art, without departing from the context or scope of the present invention.

What is claimed is:

1. Dextran derivatives of general formula $DMC_a B_b Su_c S_d$, in which:

D represents a polysaccharide chain, comprising concatenations of glucoside units, MC represented methylcarboxylate groups, B represents carboxymethylbenzylamide groups, Su represents sulfate groups, S represents sulfonate groups, a, b, c and d represent the degree of substitution (ds), expressed relative to the number of free hydroxyl functions in a dextran glucoside unit, with groups MC, B, Su and S, respectively; a being equal to 0 or $\geq 0.3$, b being equal to 0 or $\geq 0.1$, c being equal to 0 or $\leq 0.1$ and d being equal to 0 or $\leq 0.15$, with the proviso that when d=0, a and/or b are $\neq 0$, which products display:

homogeneity of the size distribution of the chains, illustrated by an elution profile of symmetrical Gaussian type in high performance steric exclusion chromatography, and homogeneity of the distribution of charged chemical groups, illustrated by an elution profile as a single symmetrical peak in low pressure ion exchange chromatography.

2. Dextran derivatives of general formula $DMC_a B_b Su_c S_d$, according to claim 1, characterized in that $a \geq 0.6$, $b \neq 0$, c equal to 0 or $\leq 0.5$ and $d \leq 0.05$ or equal to 0 and in that their molar mass is between 3000 and 500,000 g/mol.

3. Dextran derivatives of general formula $DMC_a B_b Su_c S_d$, according to claim 1, characterized in that $a \geq 0.3$, $b \neq 0$, c equal to 0 or $\leq 0.4$ and $d \leq 0.15$ or equal to 0 and in that their molar mass is between 10,000 and 60,000 g/mol.

4. Dextran derivatives of general formula $DMC_a B_b Su_c S_d$, according to claim 1, characterized in that $a \geq 0.5$, $b \neq 0$, c equal to 0 or $\leq 0.4$ and $d \leq 0.15$ or equal to 0 and in that their molar mass is between 3000 and 100,000 g/mol.

5. Dextran derivatives of general formula $DMC_a B_b Su_c S_d$, according to claim 1, characterized in that $a \geq 0.4$, $b \neq 0$, $c \geq 0.3$ and $d \leq 0.15$ or equal to 0 and in that their molar mass is between 3000 and 20,000 g/mol.

6. A medicine comprising, as an active principle, at least one dextran derivative according to claim 1.

7. Process for preparing dextran derivatives of general formula $DMC_a B_b Su_c S_d$, according to claim 1, comprising the following steps:

a) carboxymethylation comprising (i) activation of an unsubstituted dextran, by placing said dextran in contact with a basic two-phase liquid aqueous-alcoholic medium for at least 1 hour with stirring, (ii) addition of monochloroacetic acid to the activated product obtained, at a temperature of between 40 and 90° C., preferably at 60° C., the ratio RMC, equal to the number of moles of monochloroacetic acid/number of moles of OH, being between 0.3 and 2, (iii) isolation and optionally purification of the dextran methylcarboxylate (DMC) obtained;

b) coupling of benzylamine with methylcarboxylate groups comprising (i) the placing in contact, for at least 2 hour and in an acidic aqueous medium, of the DMC obtained in a) with benzylamine, in the presence of a water-soluble carbodiimide as coupling agent, at a temperature of between 0° C. and 30° C., the CMC/MC molar ratio being between 0.25 and 2 and the benzylamine/MC molar ratio being between 0.25 and 2, (ii) isolation of the dextran methylcarboxyl benzylamide (DMCB) obtained and optionally purification thereof, c) sulfation comprising (i) the formation of a trialkylammonium salt of the DMCB obtained in b), (ii) solubilization of the salt obtained in an anhydrous polar solvent, generally a Lewis base, and (iii) addition, to said dissolved salt, of a complex based on sulfur trioxide such as $SO_3$-pyridine, $SO_3$-triethylamine or $SO_3$-DMF dissolved in the same solvent, at a temperature of less than 70° C., the complex based on sulfur trioxide/free OH molar ratio being between 0.25 and 12; and, optionally, d) sulfonation of the groups B by mixing, with stirring, a derivative DMCBSu in suspension in an anhydrous solvent with chlorosulfonic acid dissolved in the same solvent, at a temperature between room temperature and the boiling point of the solvent used.

8. Process according to claim 7, characterized in that, in step a), the water alcohol ratio in said two phase liquid aqueous-alcoholic medium is between 10/90 v/v and 25/75 v/v.

9. Process according to claim 7 characterized in that the water-soluble carbodiimide from step b) is selected from the group consisting of 1-cyclohexyl-3-(2-morpholinoethyl) carbodiimide meta-p-toluene sulfonate (CMC) and 1-ethyl-3-(3-dimethyl-aminopropyl)carbodiimide hydrochloride (EDC).

10. Methylcarboxydextran benzylamide (DB).

11. A medicine as claimed in claim 6 further comprising at least one additional active principal selected from the group consisting of an acidic fibroblast growth factor (FGF) and a basic fibroblast growth factor (FGF).

12. A medicine as claimed in claim 6 further comprising at least one member of the group consisting of at least one pharmaceutically acceptable vehicle and a physiologically acceptable support.

13. A process as claimed in claim 7 wherein said Lewis base is at least one member selected from the group consisting of dimethyl sulfoxide (DMSO) and dimethylformamide (DMF).

14. A process as claimed in claim 8 wherein said water alcohol ratio in said two phase liquid aqueous-alcoholic medium is about 15/85 v/v.

* * * * *